(12) United States Patent  
Govorun et al.

(10) Patent No.: US 9,376,705 B2  
(45) Date of Patent: Jun. 28, 2016

(54) METHOD FOR DETECTING SUSCEPTIBILITY OF MICROORGANISMS TO CHEMICAL AGENTS

(71) Applicant: Idmic SA, Ecublens (CH)

(72) Inventors: Vadim Govorun, Moscow (RU); Elena Ilina, Moscow (RU); Alexei Podoplelov, Pfaffikon (CH)

(73) Assignee: Idmic SA, Ecublens (CH)

( * ) Notice: Subject to any disclaimer, the term of this patent is extended or adjusted under 35 U.S.C. 154(b) by 0 days.

(21) Appl. No.: 14/406,303

(22) PCT Filed: Jun. 6, 2013

(86) PCT No.: PCT/EP2013/061719  
§ 371 (c)(1),  
(2) Date: Dec. 8, 2014

(87) PCT Pub. No.: WO2013/182647  
PCT Pub. Date: Dec. 12, 2013

(65) Prior Publication Data  
US 2015/0191764 A1   Jul. 9, 2015

(30) Foreign Application Priority Data  
Jun. 6, 2012   (CH) ...................................... 0785/12

(51) Int. Cl.  
*C12Q 1/04* (2006.01)  
*C12Q 1/18* (2006.01)

(52) U.S. Cl.  
CPC .............. *C12Q 1/18* (2013.01); *G01N 2333/24* (2013.01); *G01N 2333/245* (2013.01); *G01N 2560/00* (2013.01)

(58) Field of Classification Search  
None  
See application file for complete search history.

(56) References Cited

U.S. PATENT DOCUMENTS

2008/0009029 A1   1/2008   Govorun et al.

FOREIGN PATENT DOCUMENTS

| EP | 2 267 459 A1 | 12/2010 |
| WO | WO 2007135385 A1 * | 11/2007 |
| WO | 2011/154517 A1 | 12/2011 |

OTHER PUBLICATIONS

Kempf "Rapid Detection of Carbapenem Resistance in Acinetobacter baummannii Using Matrix-Assisted Laser Desorption Ionization-Time of Flight Mass Spectrometry", PLoS One, Feb. 2012, vol. 7, Issue 2, e31676, 1-8.*

Sparbier "Matrix-Assisted Laser Desorption Ionization—Time of Flight Mass Spectrometry-Based Functional Assay for Rapid Detection of Resistance against β-Lactam Antibiotics", Journal of Clinical Microbiology, 2011, 927-937.*

Ron "Bacterial Stress Response", Chapter 16, The Prokaryotes-Prokaryotic Physiology and Biochemistry, Springer-Verlag, Berlin, 2013.*

(Continued)

*Primary Examiner* — Robert Yamasaki  
*Assistant Examiner* — Charles Zoltan Constantine  
(74) *Attorney, Agent, or Firm* — Sughrue Mion, PLLC

(57) ABSTRACT

A method for detecting susceptibility of microorganisms to chemical agents or antibiotics through a combination of exposing the microorganisms to the chemical agents or antibiotics after having exposed the microorganisms to a stress response-inducing stimulus and subsequently analyzing the response of the microorganisms by mass spectrometry.

21 Claims, 4 Drawing Sheets

(56) References Cited

OTHER PUBLICATIONS

Extraction, obtained from Student Website for Organic Chemistry, 3rd Edition, Marye Anne Fox; available at physicalscience.jbpub.com/orgo/interactive_glossary_showterm.cfm?term=Extraction, Copyright 2015.*

Acid-Base Extraction, Lab 17, p. 239-240, from Exercises for the General, Organic, & Biochemistry Laboratory, William G. O'Neal, 2015, Morton Publishing USA.*

Maxim Kalashnikov et al., "A microfluidic platform for rapid, stress-induced antibiotic susceptibility testing of *Staphylococcus aureus*," Lab on a Chip, 2012, pp. 4523-4532, vol. 12, No. 21.

International Search Report of PCT/EP2013/061719 dated Feb. 18, 2014.

Written Opinion of the International Searching Authority of PCT/EP2013/061719 dated Feb. 18, 2014.

* cited by examiner

METHOD FOR DETECTING SUSCEPTIBILITY OF MICROORGANISMS TO CHEMICAL AGENTS

CROSS REFERENCE TO RELATED APPLICATIONS

This is a National Stage of International Application No. PCT/EP2013/061719 filed Jun. 6, 2013, claiming priority based on Swiss Patent Application No. 00785/12 filed Jun. 6, 2012, the contents of all of which are incorporated herein by reference in their entirety.

TECHNICAL AREA

The present invention relates to a method in the area of medical microbiology for detecting susceptibility of microorganisms to chemical agents or antibiotics, comprising a quantity of microorganisms incubated within a liquid nutrient medium together with a quantity of chemical agent or antibiotic added to the nutrient medium. After removing the microorganisms from the incubated nutrient medium the proteins and/or peptides from the supernatant are extracted, isolated and processed for mass spectrometric analysis, according to the features of the preamble of claim 1.

STATE OF THE ART

Methods for measuring the susceptibility of microorganisms to chemical agents or antibiotics are known in bacteriology and epidemiology in which microorganisms are analyzed in a known manner using mass spectrometry. Chemical agents or antibiotics to be tested are added to a microorganism containing nutrition medium which may exert effects on microbial growth. Using mass spectrometry, microbial susceptibility to chemical agents and antibiotics may be analyzed in a cheap and easy manner.

In US 2008/0009029 A1 a method is disclosed in which microorganisms, particularly bacteria, are identified and characterized on the basis of a mass spectrometric measurement of their protein profiles with ionization by matrix-assisted laser deposition. In order to measure the microbial resistance to antibiotics, the protein profiles of microorganisms are measured after cultivation for a short time duration in nutrient media containing the antibiotics.

WO 2011/154517 A1 relates to the determination of resistances of microorganisms which produce β-lactamases, in particular "extended spectrum β-lactamases". The document describes a method whereby the microbial resistance can be measured by means of catalytic effect of the microbially produced β-lactamases on β-lactam antibiotics, which consists in a hydrolytic cleavage of the β-lactam ring. The method determines the resistance of the bacteria a few hours after a suitable substrate, either a β-lactam antibiotic or a customized β-lactam derivate, has been added to the suspension of the microbe, by direct mass spectrometric measurement of the substrate breakdown caused by the β-lactamases.

SUMMARY OF THE INVENTION

Based on the prior art it is an object of the present invention to provide a method which can rapidly measure the susceptibility of microorganisms to chemical agents or antibiotics, which advantageously allows latter chemical agent or antibiotic to be analyzed not only on its bacteriolytic, but also on its bacteriostatic properties.

In the context of the present invention, the words "microbe" and "microorganism" are used interchangeably. Analogously, the word "microbial" is interpreted as "of microbes" or "of microorganisms".

In the context of the present invention, the word "cell suspension" refers to microbial cells in a liquid nutrient medium.

In the context of the present invention, the words "reference mass spectrum for the microorganism" relate to a mass spectrum obtained for the same microorganism under the same conditions but without exposition to a stress response-inducing stimulus such as an antibiotic or chemical agent.

In the context of the present invention, the word "enhancer" refers to a stress response-inducing stimulus that is a chemical stimulus.

The object of the present invention is reached through a method with properties listed in claim 1, wherein microorganisms are cultured in a nutrient medium and being exposed to a stress response-inducing stimulus which can be a chemical or a physical stimulus for a certain time followed by processing of the medium in which microorganism fragments may be dispensed due to cell lysis, and following that, the microorganism-free supernatant is analyzed on its protein and/or peptide components and compared to control samples and/or other reference samples.

The object of the present invention is further reached through a method with properties listed in claim 2, wherein microorganisms are cultured in a nutrient medium together with an enhancer and a chemical agent or antibiotic for a certain time followed by processing of the medium in which microorganism fragments may be dispensed due to cell lysis, and following that, the microorganism-free supernatant is analyzed on its protein and/or peptide components and compared to control samples and/or other reference samples.

The method comprises the addition of a quantity of microbial cells, i.e. cells of a microorganism, to a liquid nutrient medium and exposing the cells to a stress response-inducing stimulus which can be a chemical stimulus (a substance) or can be a physical stimulus like an electric field, magnetic field, temperature change or radiation dose.

In the case the stress-response-inducing stimulus is a chemical stimulus (an enhancer), the method comprises the addition of a quantity of microbial cells, i.e. cells of a microorganism, to a liquid nutrient medium supplemented with a quantity of an enhancer specific for a certain group (genus or family) of microorganisms as well as for a certain chemical agent or antibiotic.

The microbial cells or cells of microorganisms may be obtained for example from a medical sample to be analyzed, such as for example blood, urine, mucus, or saliva, or from a sample of soil or water and/or may be cultured by conventional bacteriological methods.

In the case the stress-response-inducing stimulus is a chemical stimulus (an enhancer), the microorganisms in the nutrient medium are pre-incubated at a predetermined temperature for a predetermined time in the presence of a stress-response inducing stimulus, i.e. an enhancer. After addition of a quantity of antibiotic to the nutrient medium, the microorganisms are again incubated at a predetermined temperature for a predetermined time. The cells are removed from the incubated nutrient medium to yield the supernatant. The proteins within the supernatant are extracted by adding alcohol followed by isolation of the extracted proteins for example by sedimentation in a centrifuge. A quantity of a solvent is added to the extracted protein, i.e. the sediment, for mass spectrometric analysis and a quantity of the solution is added and dried on a mass spectrometric sample support to yield a mass spectrometric sample. Finally a mass spectrum of the sample is acquired and compared to at least one reference mass spectrum.

The present invention allocates a method for detecting susceptibility of microorganisms to chemical agents or antibiotics, such as penicillin derivates (penams) (e.g. ampicillin), cephalosporins (cephems) (e.g. ceftriaxon, cefixime) or carbapenems (e.g. imipenem, meropenem) whereby between 1 and 100 colonies of microorganisms, preferably between 5 and 50 and most preferably around 10 colonies of microorganisms are added to 1 mL of liquid nutrient medium to form a cell suspension.

The microorganisms used in this method are comprised of Gram-negative bacteria, and in particular of the Enterobacteriaceae family bacteria (*Salmonella, Escherichia coli, Yersinia pestis, Klebsiella, Shigella, Proteus, Enterobacter, Serratia, Citrobacter* etc.), *Pseudomonas aeruginosa* or *Acinetobacter* ssp, however, any other kind of microorganism may be used depending on the chemical agent or antibiotic to be tested. The liquid medium in this case constitutes a Müller-Hinton broth, which may be replaced by any other type of medium or broth depending on the type of microorganism. The turbidity of the microorganisms dispensed in the liquid nutrient medium is between 0.3 and 0.7, more precisely between 0.4 and 0.6, preferably at 0.5 on McFarland standards, corresponding to approximately $1.5 \times 10^8$ colony forming units/mL.

For susceptibility testing of microorganisms used in the method described herein, any stress response-inducing chemical stimulus that induces a stress response in the tested microorganism may be used as an enhancer. For example, enhancers that induce an osmotic, metabolic, oxidative, pH (acidic or basic), or salinity stress response in a certain group (genus or family) of microorganisms at certain concentrations, may be used as enhancers.

Exemplary enhancers that induce an oxidative stress response are enhancers that induce the formation of reactive oxygen species in either the microorganism itself or the liquid nutrient medium.

Specifically for susceptibility testing of Enterobacteriaceae family bacteria to β-lactam antibiotics, water-soluble salts of malic acid or ascorbic acid such as for example sodium malate or sodium ascorbate are used as enhancer, which have to be replaced by other enhancers for susceptibility testing of other bacterial family to other chemical agents. Preferably the water-soluble salt of malic acid or ascorbic acid such as sodium malate or sodium ascorbate in a certain quantity and concentration is added to the liquid nutrient medium, which may have to be adjusted in quantity and concentration for other enhancers concerning other families of microorganisms. In the case the enhancer is a water-soluble salt of malic acid or ascorbic acid, the enhancer is added to the liquid nutrient medium such as to yield an enhancer concentration of from about 0.025 to 0.125 mM. in particular of from about 0.1 to about 0.15 mM, In the case the stress-response-inducing stimulus is a physical stimulus like an electric field, magnetic field, temperature change or radiation dose, the method comprises the addition of a quantity of microbial cells, i.e. cells of a microorganism, to a liquid nutrient medium and subsequently exposing the cells to certain quantity of the physical stimulus. In the case of a radiation dose, electric or magnetic field, the intensity and duration will have to be adjusted, whereas in the case of a temperature change the absolute change and duration will depend strongly on the tested microorganism.

The microbial cells to form a cell suspension may be obtained from a medical sample to be analyzed, such as for example blood, urine, mucus, or saliva, or from a sample of soil or water and/or may be cultured by conventional bacteriological methods.

In the case where the microorganisms used in this method are comprised of Gram-negative bacteria, and in particular of the Enterobacteriaceae family bacteria, the cell suspension is pre-incubated at standard cell cultivation conditions, more precisely at 37° C., which may differ in temperature for other types of microorganisms. Preferably the incubation is carried out in a temperature-controlled orbital shaker, operating at for example 280 rpm.

A chemical agent or an antibiotic equal to the threshold level of the given microorganism according to the Clinical and Laboratory Standards Institute (CLSI) is added to the cell suspension and incubated under standard cultivation conditions, more precisely at 37° C., which again may differ in temperature for types of microorganisms.

For example, threshold levels for Ampicillin and Cetriaxon are 16 mg/L, and are 2 mg/L for Meropenem.

The microorganisms are precipitated by centrifugation or any other means of precipitation followed by the collection of the supernatant. The proteins within the supernatant are extracted by addition of an alcohol, preferably having a temperature of −20° C., preferably by addition of ethanol to the supernatant in a manner known in the art. The extracted proteins are then precipitated by centrifugation or any other means of precipitation, followed by the collection of the sediment, i.e. the sediment of extracted proteins.

The precipitation of the microorganisms may be preceded by the addition of a surfactant such as for example sorbitan monooleate.

To process the obtained sediment for a mass spectrometric sample, the sediment is rinsed in alcohol, preferably ethanol, dissolved in an acid, preferably in formic acid, followed by the addition of cyanide, preferably of acetonitrile, followed by centrifugation. To produce a mass spectrometric sample, sediment solution together with a matrix solution is applied to the mass spectrometric sample support and dried.

A mass spectrum of the set of proteins on the mass spectrometric sample support is acquired using the MALDI time-of-flight mass spectrometer in linear mode. The obtained mass spectrum is then compared to mass spectra of a control sample or other samples.

Further embodiments are specified in the dependent claims.

BRIEF DESCRIPTION OF THE FIGURES

Preferred embodiments of the invention are described in the following on the basis of the figures which merely serves as an explanation and are not interpreted to be restrictive. The figures show.

PREFERRED EMBODIMENTS

Figure 1:
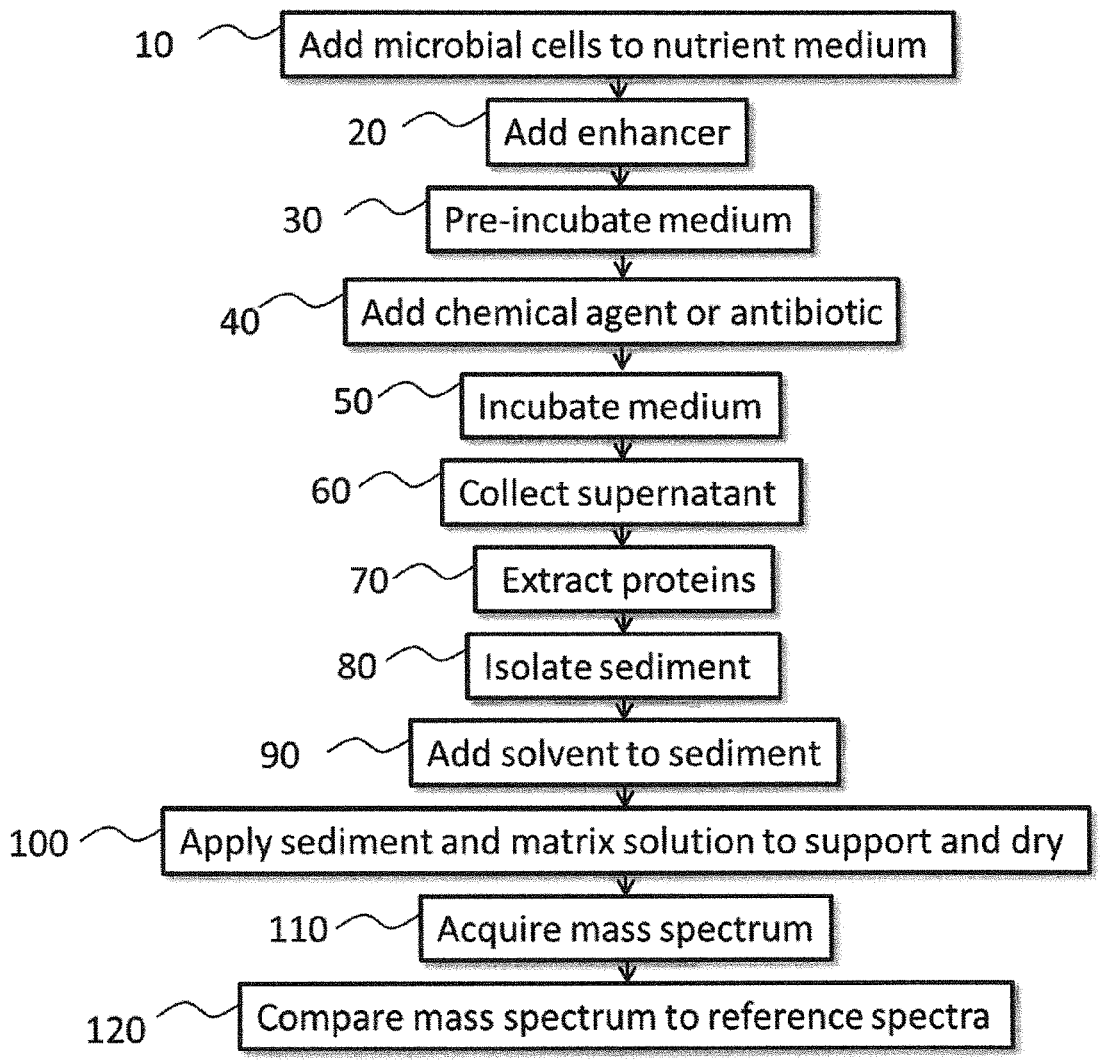
FIG. 1 shows a process flowchart illustrating the steps in an illustrative process for determining the susceptibility of microorganisms to chemical agents or antibiotics in accordance with the principles of the invention.

FIG. 1 shows a preferred embodiment of a method according to the present invention for detecting susceptibility of microorganisms to chemical agents or antibiotics.

In a first process step 10, approximately ten colonies of microorganisms of the bacterial type Enterobacteriaceae are added to 1 mL of a liquid Müller-Hinton broth nutrient medium. The turbidity of the microorganisms in the liquid nutrient medium is 0.5 on McFarland standards, corresponding to approximately $1.5 \times 10^8$ colony forming units/mL.

In a second process step 20, 5 µL of 5-25 mM, especially 25 mM of a water-soluble salt of malic acid or ascorbic acid, for example sodium malate as an enhancer for Enterobacteriaceae family bacteria is added into the liquid nutrient medium. The enhancer may also be added into the liquid nutrient medium in solid form.

In a third process step 30, the microorganisms in the nutrient medium are pre-incubated at 37° C. for 30 minutes.

In a fourth process step 40, a quantity of a chemical agent or antibiotic equal to the threshold level of the given microorganism according to the Clinical and Laboratory Standards Institute is added to the microorganisms in the liquid nutrient medium.

In a fifth process step 50, the microorganisms in the nutrient medium are incubated at 37° C. for 60 minutes.

In a sixth process step 60, the microorganisms are removed from the nutrient medium by centrifugation at 10'000 g or 15'000 g for 5 minutes at room temperature. The remaining supernatant is collected in a new experimental tube.

In a seventh process step 70, all proteins within the supernatant are extracted by adding 400 µL supernatant to 900 µL ethanol at −20° C., followed by incubation at −20° C. for 1 hour.

In an eighth process step 80, the extracted proteins are centrifuged at 15'000 g for 20 minutes to yield protein sediment which is further rinsed with 70% ethanol.

In a ninth process step 90, a solvent comprising 5 µL 70% formic acid and 5 µL acetonitrile is added to the sediment solution, followed by centrifugation for 2 minutes at 15'000 g.

In a tenth process step 100, 1 µL sediment solution together with 1 µL matrix solution composed of a saturated solution of α-cyano-4-hydroxycinnamic acid in compound of 50% acetonitrile and 2.5% trifluoroacetic acid is added to the mass spectrometric sample support and dried to produce a mass spectrometric sample.

In an eleventh process step 110, a mass spectrum of the sample is acquired in the range of 2'000-20'000 m/z using the MALDI time-of-flight mass spectrometer in linear mode measuring.

In a twelfth process step 120, the obtained mass spectrum of the sample is compared to the mass spectrum of at least one reference spectrum or control sample.

Figure 2:
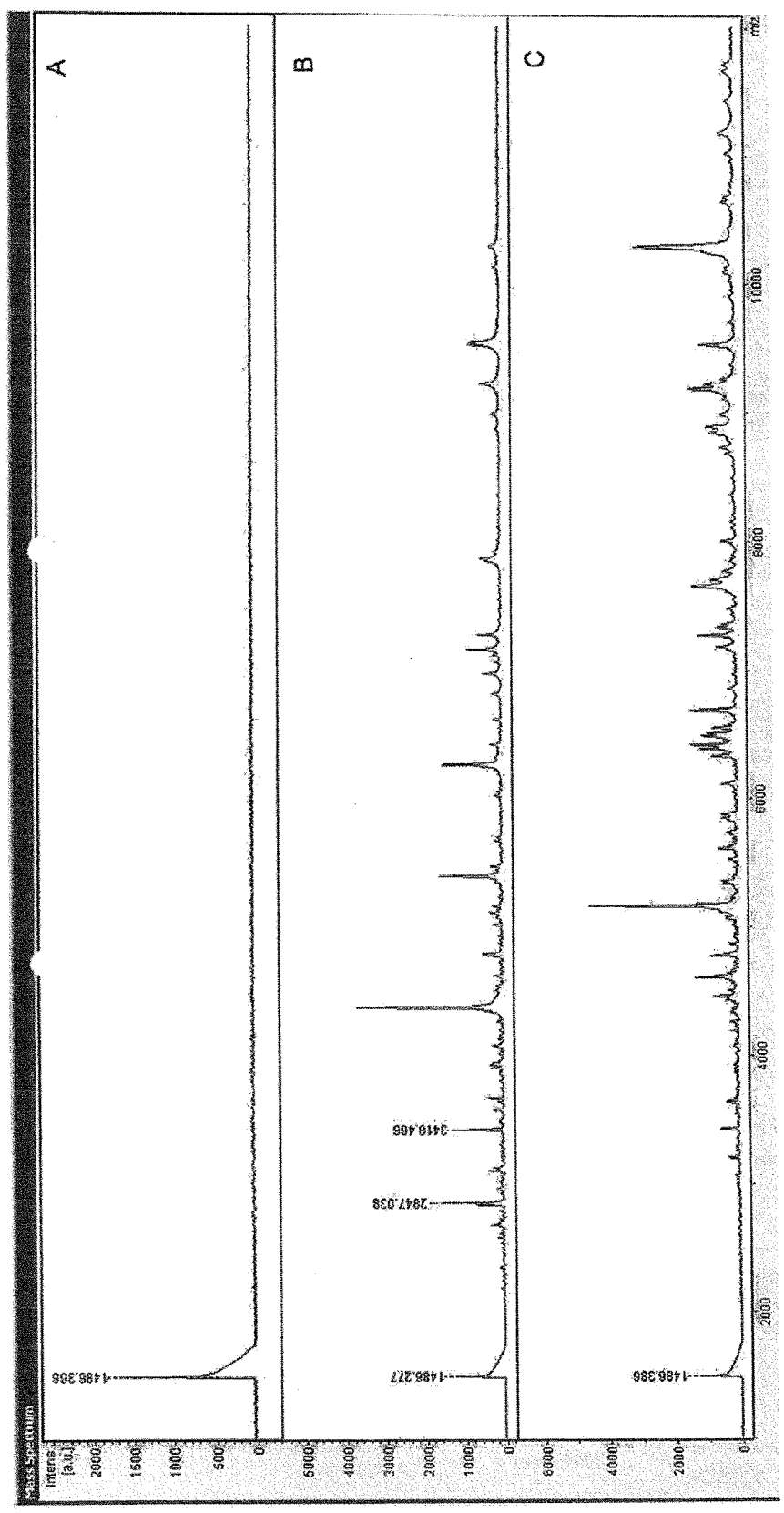
FIG. 2 shows the mass spectra collected for supernatants obtained during the testing of a *Escherichia coli* strain susceptible to ampicillin and ceftriaxon: (Top)—spectrum of the control sample supernatant; (Middle)—spectrum of the experimental sample supernatant after treatment with 8 mg/L ampicillin; (Bottom)—Spectrum of the experimental sample supernatant after the treatment with 8 mg/L ceftriaxone. The non-resistant type of *Escherichia coli* has been destroyed which creates a specific protein profile.

FIG. 2 shows the mass spectra collected for supernatants obtained during the testing of a *Escherichia coli* strain susceptible to ampicillin and ceftriaxone. The uppermost spectrum A shows the signal intensity in arbitrary units (a.u.) against the mass-to-charge ratio, m/z in Da/e for a spectrum of the control sample supernatant without any signal (a common signal at approximately 1500 Dale reflects a start of measuring). The spectrum shown below the control spectrum shows the experimental sample supernatant after treatment with 8 mg/L ampicillin as spectrum B with a lot of peaks other than 1500 Da/e. The bottommost spectrum C shows the experimental sample supernatant after the treatment with 8 mg/L ceftriaxone. In both cases the non-resistant type of *Escherichia coli* has been destroyed, so the spectrum B as well as spectrum C contains signals from any proteins and peptides accumulated in nutrient medium during the death of bacteria.

Figure 3:
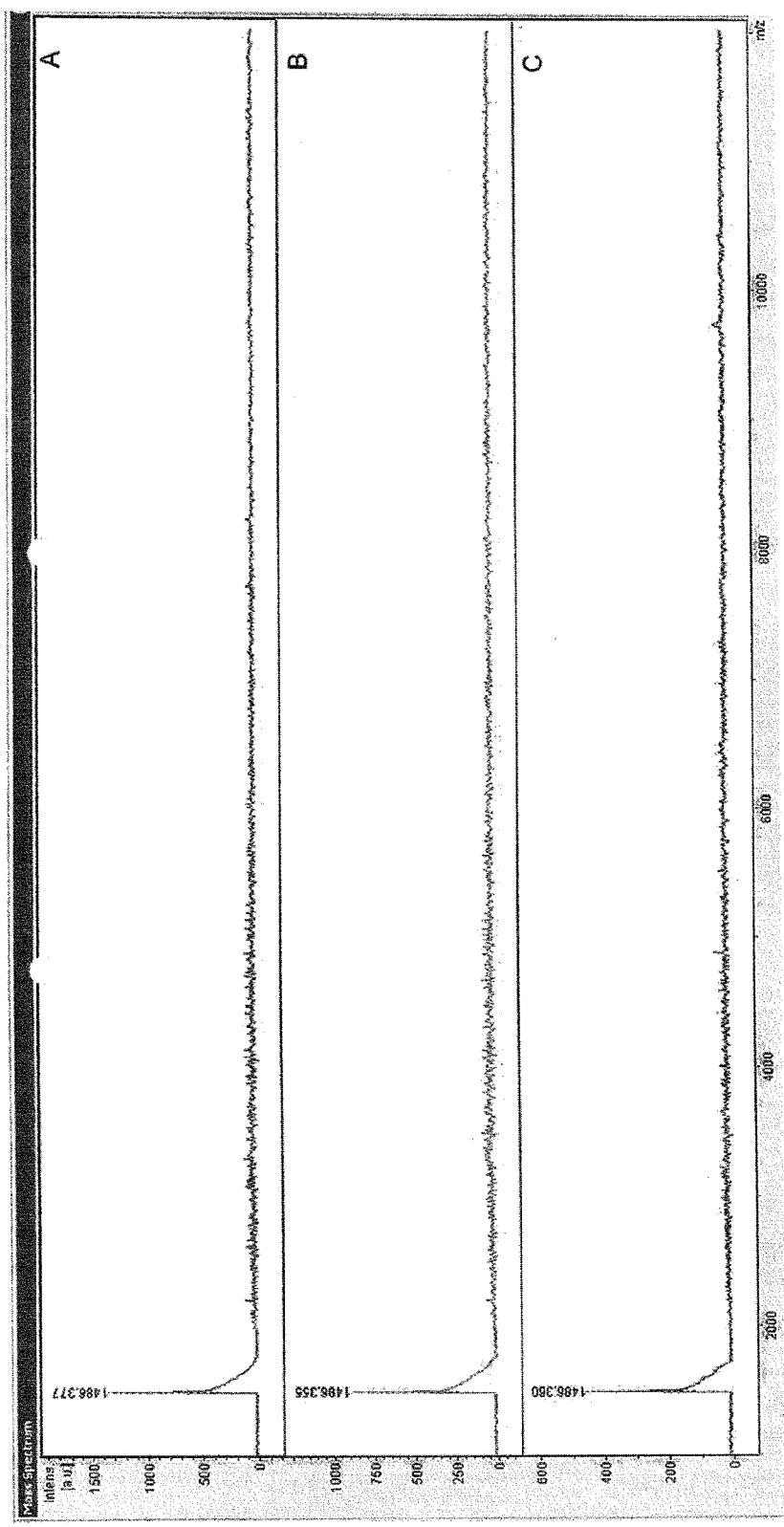
FIG. 3 shows the mass spectra collected for supernatants obtained during the testing of a *Escherichia coli* strain resistant to ampicillin and ceftriaxon: (Top)—spectrum of the control sample supernatant; (Middle)—spectrum of the experimental sample supernatant after treatment with 8 mg/L ampicillin; (Bottom)—Spectrum of the experimental sample supernatant after the treatment with 8 mg/L ceftriaxone.

FIG. 3 shows the mass spectra collected for supernatants obtained during the testing of a *Escherichia coli* strain resistant to ampicillin and ceftriaxone. Top spectrum A shows the control sample supernatant, followed by the spectrum B in the middle of the experimental sample supernatant after treatment with 8 mg/L ampicillin, and finally concluded by the bottom spectrum C of the experimental sample supernatant after the treatment with 8 mg/L ceftriaxone. All shows a common peak at approximately 1500 Da/e reflects a start of measuring and no further significant signal.

Figure 4:
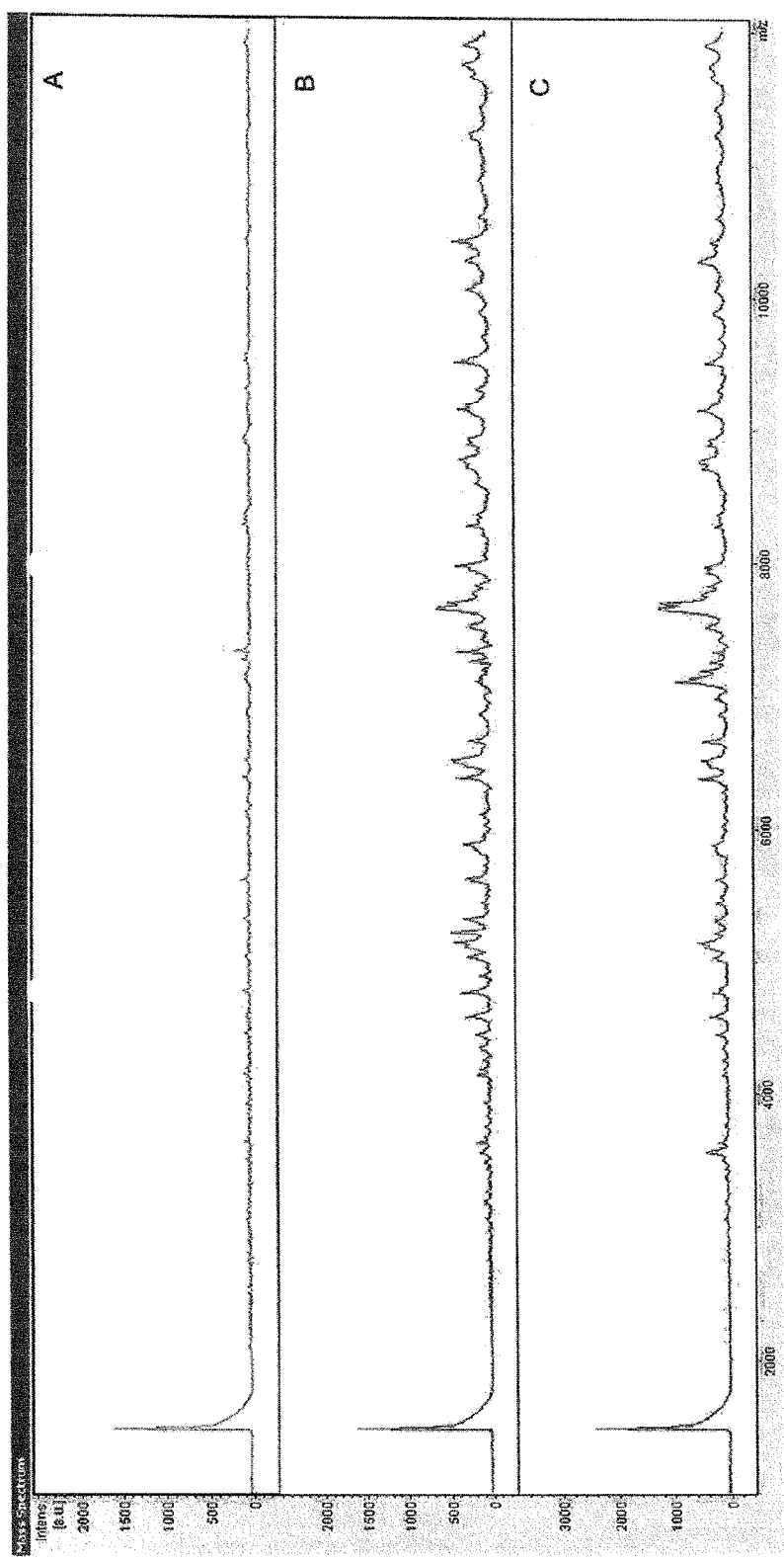
FIG. 4 shows the mass spectra collected for supernatants obtained during the testing of a *Citrobacter* ssp strain susceptible to ampicillin and ceftriaxon: (Top)—spectrum of the control sample supernatant; (Middle)—spectrum of the experimental sample supernatant after treatment with 8 mg/L ampicillin; (Bottom)—Spectrum of the experimental sample supernatant after the treatment with 8 mg/L ceftriaxone. The non-resistant type of *Citrobacter* ssp has been destroyed which creates a specific protein profile.

FIG. 4 shows the mass spectra collected for supernatants obtained during the testing of a *Citrobacter* ssp strain susceptible to ampicillin and ceftriaxone. As usual the top spectrum A shows the control sample supernatant. Here, the middle spectrum B shows the experimental sample supernatant after treatment with 8 mg/L ampicillin and bottom spectrum C shows the experimental sample supernatant after the treatment with 8 mg/L ceftriaxone. In both cases the non-resistant type of *Citrobacter* ssp has been destroyed, so the spectrum B as well as spectrum C contains signals from any proteins and peptides accumulated in nutrient medium during the death of bacteria.

| REFERENCE SIGN LIST | |
|---|---|
| 10 | Process step 01 |
| 20 | Process step 02 |
| 30 | Process step 03 |
| 40 | Process step 04 |
| 50 | Process step 05 |
| 60 | Process step 06 |
| 70 | Process step 07 |
| 80 | Process step 08 |
| 90 | Process step 09 |
| 100 | Process step 10 |
| 110 | Process step 11 |
| 120 | Process step 12 |

The invention claimed is:
1. A method for determining the susceptibility of a microorganisms to chemical agents or antibiotics, comprising:
 (a) adding a quantity of microbial cells to a liquid nutrient medium;
 (b) exposing the microbial cells to a chemical or a physical stimulus capable of inducing a stress response, thereby inducing a stress response;
 (c) pre-incubating the microbial cells in the nutrient medium at a temperature for a time;

(d) adding a quantity of a chemical agent or antibiotic to the liquid nutrient medium;

(e) incubating the microbial cells at a temperature for a time;

(f) removing the microbial cells from the incubated nutrient medium and collecting the supernatant;

(g) precipitating the proteins from the supernatant with alcohol;

(h) isolating the precipitated protein from the alcohol treated supernatant;

(i) adding a quantity of a solvent to the isolated protein to dissolve the isolated protein for mass spectrometric analysis;

(j) applying the dissolved protein and a matrix solution to a mass spectrometric sample support and drying the mixture of dissolved protein and matrix solution on the sample support to produce a mass spectrometric sample;

(k) acquiring a mass spectrum of the mass spectrometric sample; and (l) comparing the acquired mass spectrum with at least one reference mass spectrum for the same microorganism to determine the susceptibility of the microorganism to the chemical agent or antibiotic.

2. The method of claim 1, wherein the stimulus capable of inducing a stress response is a chemical stimulus and step (b) comprises adding a quantity of a chemical stimulus specific for a certain group, genus, or family of microorganisms to the liquid nutrient medium.

3. The method of claim 1, wherein step (a) comprises adding about 10 microbial cell colonies to 1 mL of liquid nutrient medium.

4. The method of claim 3, wherein the liquid nutrient medium consists of a Müller-Hinton broth.

5. The method of claim 3, wherein the turbidity of the microbial cells in the liquid nutrient medium is 0.5 on McFarland standards, corresponding to approximately $1.5 \times 10^8$ colony forming units/mL.

6. The method according to any one of claims 2 to 5, wherein at step (b) sodium malate or sodium ascorbate is used as the chemical stimulus for Enterobacteriaceae family bacteria.

7. The method according to claim 2, wherein at step (b) a water-soluble salt of malic acid or ascorbic add, is the chemical stimulus for Enterobacteriaceae family bacteria.

8. The method according to claim 2, wherein in step (b) 5 µL of a 25 mM solution of sodium malate is the chemical stimulus for Enterobacteriaceae family bacteria.

9. The method according to claim 1, wherein step (c) comprises pre-incubating the microbial cells in the nutrient medium for 30 minutes at 37° C.

10. The method according to claim 1, wherein step (d) consist of adding a quantity of an antibiotic to the liquid nutrient broth to obtain a level equal to the threshold level according to the Clinical and Laboratory Standards institute for the species of microorganism being tested.

11. The method according to claim 1, wherein step (e) comprises incubating the microbial cells for 60 minutes at 37° C.

12. The method according to claim 1, wherein step (f) comprises removing the microorganisms by centrifugation for 5 minutes at 10,000 g or 15,000 g at room temperature and collecting the supernatant.

13. The method according to claim 1, wherein at step (g) ethanol is used as the alcohol, and wherein at step (g) 400 µL of the supernatant is mixed with 900 µL ethanol having a temperature of −20° C., and the resulting mixture is incubated for 1 hour at −20° C., and is centrifuged for 20 minutes at 15,000 g following incubation.

14. The method according to claim 1, wherein at step (i) the precipitated protein is washed in 70% ethanol, the washed protein is dissolved in 5 µL 70% formic acid, and 5 µL acetonitrile is added to the dissolved protein, followed by centrifugation for 2 minutes at 15,000 g.

15. The method according to claim 1, wherein step (j) comprises applying 1 µL of dissolved protein and 1 µL of matrix solution to the mass spectrometric sample support.

16. The method according to claim 1, wherein the matrix solution is a saturated solution of α-cyano-4-hydroxycinnamic acid dissolved in an aqueous solution of 50% acetonitrile and 2.5% trifluoroacetic acid.

17. The method according to claim 1, wherein step (k) comprises an acquisition of mass spectrum in the range of 2,000-20,000 m/z using the MALDI time-of-flight mass spectrometer in linear mode measuring.

18. The method according to claim 1, wherein in step (l) the acquired mass spectrum is compared to a mass spectrum of a control sample.

19. The method of claim 1, wherein the stimulus capable of inducing a stress response is a physical stimulus chosen from an electric field, magnetic field, temperature change or a radiation dose.

20. The method of claim 19, wherein the stress response-inducing stimulus is a temperature change.

21. The method of claim 1, wherein in step (g) the alcohol has a temperature of −20° C.

* * * * *